United States Patent [19]

March

[11] 4,217,902
[45] Aug. 19, 1980

[54] HEMOSTATIC CLIP

[76] Inventor: Alfred L. March, 889 NE. 125 St., North Miami, Fla. 22161

[21] Appl. No.: 966,293

[22] Filed: Nov. 14, 1978

Related U.S. Application Data

[63] Continuation of Ser. No. 793,047, May 2, 1977, abandoned.

[51] Int. Cl.$^3$ .............................................. A61B 17/08
[52] U.S. Cl. .................................... 128/325; 128/337
[58] Field of Search ................... 128/325, 334 R, 335, 128/336, 337, 346; 24/259 R, 20 EE, 20 W, 20 CW, 256, 255 R

[56] References Cited

U.S. PATENT DOCUMENTS

| | | | |
|---|---|---|---|
| 1,728,316 | 9/1929 | Von Wachenfeldt | 128/334 R |
| 2,307,377 | 1/1943 | Riccardi | 128/346 |
| 3,068,870 | 12/1962 | Levin | 128/346 X |
| 3,446,212 | 5/1969 | Le Roy | 128/325 |
| 3,604,425 | 9/1971 | Le Roy | 128/325 |
| 3,802,437 | 4/1974 | Kees | 128/325 |
| 3,999,555 | 12/1976 | Person | 128/321 X |

Primary Examiner—Robert W. Michell
Assistant Examiner—Michael H. Thaler
Attorney, Agent, or Firm—Gustave Miller

[57] ABSTRACT

This is a hemostatic clip for clasping the flaps of a wound together and holding them together to prevent bleeding and to promote healing until the wound is healed and in closed position, whereupon it is released. It is made in a generally tubular body form with a longitudinal slit having cooperating teeth on the slit edges. It is made of a suitable resilient metal or plastic material. Opposite the elongate slit, the tubular body is provided with an inwardly extending longitudinal U-shape depression which, when pressure is applied to the sides of the U, will cause the slit and teeth to separate, whereby it can be applied to the wound flaps. When the pressure is released, the teeth will grasp and hold the wound flaps in contact. When the wound has healed sufficiently, the pressure is again applied to release the teeth from engagement with the flaps. Ridges, eyelets or apertures are provided in the tubular body to cooperate with a pair of plyers for applying suitable pressure.

5 Claims, 11 Drawing Figures

HEMOSTATIC CLIP

This is a continuation of application Ser. No. 793,047, filed May 2, 1977, now abandoned.

BACKGROUND OF THIS INVENTION

Surgical clips, wound clasps, serrefins, etc. have been known for quite some time for holding the flaps or edges of a wound together to promote healing. They were generally made of deformable metal, not resilient, some of them being provided with teeth to catch in the wound flaps and be bent by a suitable tool to deform the metal into wound flap clasping or holding condition, and then had to be bent or deformed again to release the wound flaps. The amount of pressure they put on the wound flaps was a matter of personal skill and judgment on the part of the physician or operator in applying the clip to the wound edges, and, as such, could be overdone or underdone.

SUMMARY OF THIS INVENTION

This hemostatic clip is made of suitable resilient metal or resilient plastic, capable of being sterilized in a conventional manner, and is generally a tubular body having a longitudinal slit and has teeth extending from the slit edges. The tubular body is provided with an inverted U-shaped longitudinal portion directly opposite the longitudinal slit. This U-shaped portion is provided with pressure tool cooperating means so that when pressure is applied, the tool holds the slip open for applying the teeth and the slit edges to the flaps of the wound and are self-engaging on the wound flaps when the pressure is released.

The pressure of the teeth and slit edges on the wound flaps is predetermined by the material, size, etc. of the tubular body and is not dependent on the skill of the operator. Tool cooperating means are provided on the tubular body on opposite sides of the inverted U apex, and may be in the form of tool cooperating longitudinal ridges, which, when squeezed together, separate the teeth and slit edges.

In another form, apertures are provided in the tubular body for receiving the plyers, tool fingers and opening the slit for application to the wound flaps.

In a third form, eyelets or pockets are provided on the tubular body to receive the plyer tool for opening the flaps.

OBJECTS OF THIS INVENTION

It is an object of this invention to provide a self-attaching hemostatic clip having wound flap-engaging teeth for holding the flaps together with a pressure predetermined by the resiliency of the material.

A further object of this invention is to provide a hemostatic clip made of resilient material for applying a predetermined pressure for holding the wound flaps together.

Yet a further object of this invention is to provide a sterilizable hemostatic clip which is resilient and not deformed in operation or use.

A still further object of this invention is to provide a hemostatic clip which may be provided with different tool cooperating portions for holding it open for application to the wound flaps, the clip then being held in flap holding position by its resiliency and not by being bent or deformed in accordance with the judgment of the particular operator.

Yet a further object of this invention is to provide a reusable hemostatic clip which is never deformed in operation, and which may be sterilized for re-use.

A further object of this invention is to provide a hemostatic clip which is made of suitable sterilizable resilient metal or plastic material which is reuseable, but which is so inexpensive that it may be readily discarded after use, if desired.

Yet a further object of this invention is to provide a hemostatic clip that is an improvement over the prior art, including U.S. Pat. Nos. 733,723; 1,728,316; 2,201,610; 3,068,870; 3,446,212, amongst others.

BRIEF DESCRIPTION OF THE FIGURES

With the above and other objects in view, this invention of a hemostatic clip consists in the details of construction and combination of parts, as will be more fully understood from the following description, when read in conjunction with the accompanying drawing, in which.

DETAILED DESCRIPTION OF THIS INVENTION

Figure 1:
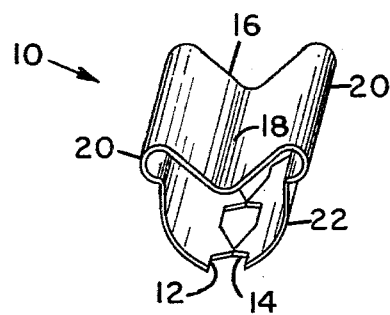
FIG. 1 is a perspective view of the preferred form of this hemostatic clip invention.
Figure 2:
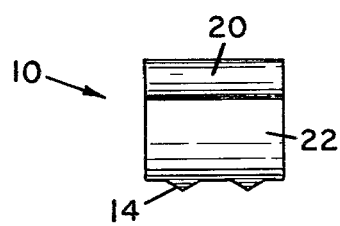
FIG. 2 is a side view of FIG. 1.
Figure 3:
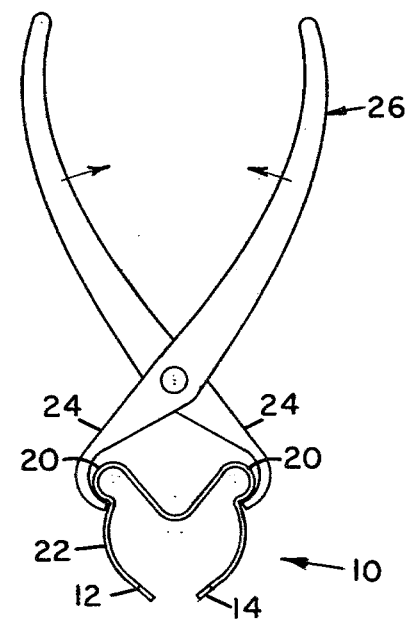
FIG. 3 is an end view of FIG. 1, together with a clip applying plyer tool.

There is shown at 10 one form of the elongate tubular body of the hemostatic clip of this invention. This clip 10 is made of suitable sterilizable resilient sheet metal or plastic material. This tubular body 10 is longitudinally slit at 12, and the slit edges 12 have opposed, slightly downwardly extending teeth 14 projecting therefrom, the resiliency of the material normally urging the teeth 14 into engaging contact. Opposite the slit edges 12, an inverted longitudinal U-shaped depression 16 is provided, having a somewhat deep apex 18. Longitudinal ridges 20 join the U-shaped portion 16 to the tubular portions 22, the apex 18 extending below the ridges 20.

These longitudinal ridges are for the purpose of cooperating with the claws 24 of a pair of crossed arm plyers 26. Due to the position of the apex 18 being below the ridges 20 squeezing the plyers 26 together with its claws 24 engaged about the ridges 20, it will cause the tubular portions 22 to move away from each other, separating the teeth 14 and slit edges 12 from each other, permitting such teeth 14 to be applied to the flaps of a sound. Then the pressure on the plyers 26 is slowly lessened, permitting the teeth 14 to be resiliently urged into wound flap engaging position. Then, with the plyer pressure completely released, the teeth 14 remain in inserted contact in the wound flaps, and the slit edges 12 press and hold the wound flaps together in healing position. When sufficient healing has taken place, the plyers 26 may be used to disengage the teeth 14 from the wound flaps and the clip is removed, either for sterilization and reuse, or for discarding.

Figure 4:
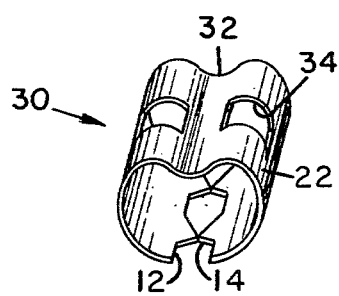
FIG. 4 is a perspective view of another form of this hemostatic clip invention.
Figure 5:
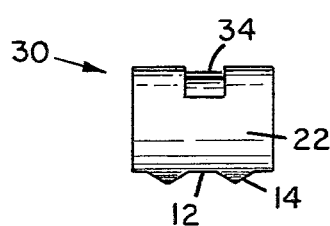
FIG. 5 is a side view of FIG. 4.
Figure 6:
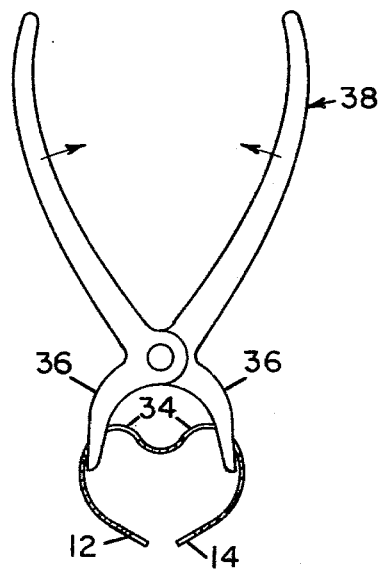
FIG. 6 is an end view of FIG. 4, together with a clip applying plyer tool therefor.
Figure 8:
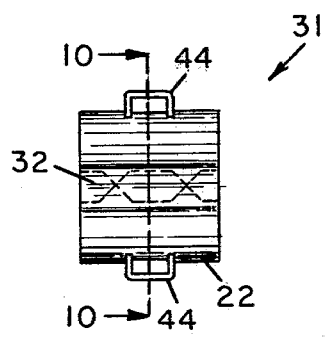
FIG. 8 is a top elevation of FIG. 7, showing open plyer tool receiving eyelets.
Figure 7:
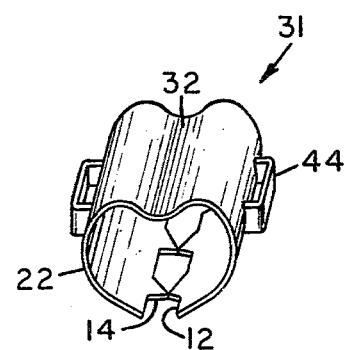
FIG. 7 is a perspective view of still another form of this hemostatic clip invention.
Figure 9:
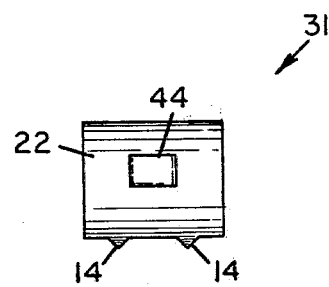
FIG. 9 is a side elevation of FIG. 8.
Figure 11:
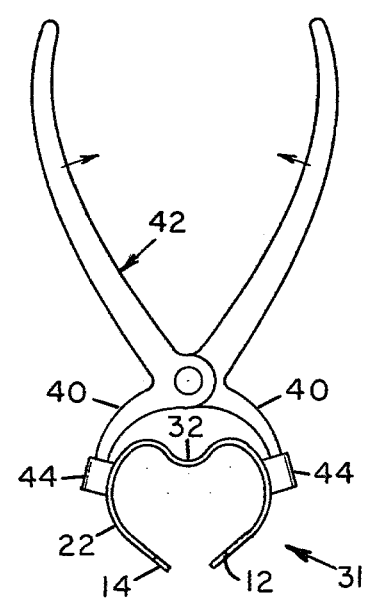
FIG. 11 is an end view of these latter forms, with a clip applying tool.
Figure 10:
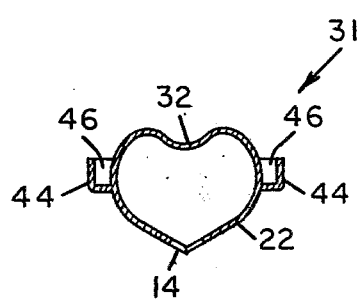
FIG. 10 is a cross section on line 10—10 of FIG. 9 but shows a plyer tool receiving pocket.

In the form shown in FIGS. 4, 5 and 6, the elongate tubular body 30 has the same tubular sides 22, the same slit edges 12, the same slightly depending teeth 14. A longitudinal depressed inverted U-shape portion 32 is provided between the tubular sides 22, and apertures 34 are provided at the juncture of the tubular side 22 and the inverted U-shaped portion 32 to receive the plyer fingers 36 of pivoted non-erosive plyer arms 38. Again, squeezing the plyer arms 38 together separates the teeth 14 and slit edges 12, permitting this clip to be applied or removed in the same manner as with the first form.

In the forms shown in FIGS. 7 through 11, the slit edges 12, the teeth 14, and the rounded tubular portions 22 of tubular body 31 are the same, and are provided with a joining inverted depressed U-portion 32, the same as in FIGS. 4, 5 and 6. Plyer fingers 40 of plyers 42 are inserted in eyelets 44 or pockets 46 on the tubular side portions 22 for applying or removing the clip to or from the wound flaps.

OPERATION OF THE INVENTION

In operation, in all forms, the plyers claws or fingers are applied about the ridges 20 or inserted in the apertures 34 or the eyelets 44 or pockets 46. In each case, squeezing the plyer handles together causes the clip to open, enabling the teeth and slit edges to be applied to the wound flaps. Slowly releasing the squeezing pressure and then withdrawing the tool leaves the clip in wound flap holding position, where it is left until healing has advanced sufficiently. The tool is then applied and its handles are squeezed to released and remove the clip, either for sterilizing and reuse, or for discarding it.

ABSTRACT OF THE DRAWING

In the drawing, like numbers refer to like parts, and for the purpose of explication, set forth below are the numbered parts of the improved hemostatic clip of this invention.

10 tubular body
12 slit edges
14 teeth
16 inverted longitudinal U-shaped depression
18 apex of 16
20 longitudinal ridges
22 tubular portions of 10
24 plyer claws
26 plyer tool
30 elongate tubular body of FIGS. 4, 5 and 6
31 elongate tubular body of FIGS. 7–11
32 inverted U-shaped portion in FIGS. 4–11.
34 apertures for receiving plyer fingers 36 in FIGS. 4, 5 and 6.
36 plyer fingers
38 non-crossing pivoted plyer arms.
40 plyer fingers
42 plyers
44 eyelets
46 pockets Although this hemostatic clip invention has been described in detail, such description is intended as being illustrative rather than limiting, since this invention may be variously embodied.

Having thus set forth and disclosed the nature of this invention, what is claimed is:

1. A hemostatic clip for applying a predetermined pressure to opposite wound flaps comprising a sheet of resilient material in the form of an elongated tubular body (10, 30, 31), wound flap engaging means (12, 14) on said tubular body, said wound flap engaging means being the edges (12) of an elongated slit extending longitudinally of said tubular body and longitudinally spaced apart teeth (14) on both slit edges extending toward each other in normal contacting relation, a portion of the periphery of said tubular body being bent radially inwardly, at a location diametrically opposite said slit, to form an upwardly open channel substantially U-shaped in cross-section and extending the entire length of the tubular body and providing an integrally formed resilient hinge section, the portions of the periphery of said tubular body on opposite sides of said channel being provided with means for receiving the jaws of a plier, whereby force may be applied to said body on opposite sides of said resilient hinge section and against the bias thereof to separate said teeth and hold them separated while applying said teeth to opposite wound flaps, and when the pressure is released, said teeth and slit edges will be resiliently biased to move the wound flaps toward contact with each other and then hold the wound flaps in predetermined pressure contact until such time as pressure is again applied to said tubular body to separate said slit edges and teeth from contact with the wound flaps to thus release the wound flaps.

2. The hemostatic clip of claim 1, wherein said means for receiving comprises an aperture in each of the portions on opposite sides of the channel.

3. The hemostatic clip of claim 1, wherein said means for receiving comprises an outwardly extending ridge formed on each said portion of the periphery which is on opposite sides of the channel.

4. The hemostatic clip of claim 1, wherein said means for receiving comprises an eyelet secured to each said portion of the periphery which is on opposite sides of the channel.

5. The hemostatic clip of claim 1 wherein said means for receiving comprises a pocket member secured to each said portion of the periphery which is on opposite sides of the channel.

* * * * *